United States Patent
Farrand et al.

(10) Patent No.: US 8,581,045 B2
(45) Date of Patent: Nov. 12, 2013

(54) **HYPERVIRULENT MUTANT OF *AGROBACTERIUM TUMEFACIENS***

(75) Inventors: Stephen K. Farrand, Seymour, IL (US); David Michael Barnhart, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 422 days.

(21) Appl. No.: 12/950,833

(22) Filed: Nov. 19, 2010

(65) Prior Publication Data

US 2011/0126324 A1    May 26, 2011

Related U.S. Application Data

(60) Provisional application No. 61/263,305, filed on Nov. 20, 2009.

(51) Int. Cl.
*C12N 15/84* (2006.01)
*C12N 1/21* (2006.01)
*A01H 5/10* (2006.01)
*C12R 1/41* (2006.01)

(52) U.S. Cl.
USPC ..... 800/294; 435/469; 435/252.2; 800/320.1; 800/300

(58) Field of Classification Search
None
See application file for complete search history.

(56) References Cited

PUBLICATIONS

Grimsley et al. (Biotechnology vol. 6 Feb. 1988, pp. 185-189).*
Tamayo et al. (Annu. Rev. Microbiol. 2007; 61: 131-148).*
Aldridge et al. (Molecular Microbiology (2003) 47(6), 1695-1708).*
Wood et al. (Science 294, 2317 (2001)).*
McCullen et al. (Annu. Rev. Cell Dev. Biol. 2006. 22:101-27).*
Luo et al., "Construction of a Derivative of *Agrobacterium tumefaciens* C58 That Does Not Mutate to Tetracycline Resistance," *Mol. Plant Microbe Interact.* 14:98-103, 2001.

* cited by examiner

*Primary Examiner* — David T Fox
*Assistant Examiner* — Jared Shapiro
(74) *Attorney, Agent, or Firm* — Klarquist Sparkman, LLP

(57) ABSTRACT

This disclosure relates to a mutant *Agrobacterium tumefaciens* that is functionally deleted for the atu1060 gene that codes for the cyclic di-GMP synthase Atu1060, as well as methods for its use in transforming plants with desired transgenes. Such bacteria are more virulent than currently used strains of *A. tumefaciens*, and thus can be used to transform a wider variety of plants, such as plants that are traditionally recalcitrant to such transformation.

21 Claims, 2 Drawing Sheets

FIG. 2

```
1         10         20         30         40         50
MQDKILLIEDSVALSMLLRTRLSDETEAEVVHCASMAEADALMQANNFTLALTG
  ↓60        70         80         90         100
LNLPDAPKGEILTLLSERKVPAIVFTATVDEEARKRYAEKKIIDYIVKDGHRTVDA
111        120        130        140        150        160
VVKTVDRIMTNKRFSVLVVDDARTARSGLVEILERQNFKVSEAHSGNRALEILSQ
           170        180        190        200        210        220
DPSIQLVITDYHMPDMDGYELTRRIRDSRSSEDLRVIGISSSTDRLLSASFLKAGAS
           230        240        250        260        270
DFVYRPFVPEELQCRIDNNIETLKQLKRLRELAERDHLTGLPNRRSFFERTRALM
           280        290        300        310        320        330
DVINDNDESGAVAILDIDHFKKINDTLGHDAGDRALKKLAELLQGMCDEQRHIP
         ↓  340        350        360        370        380
ARLGGEEFAVFLRGLDARAAYAFCEELREQVEKNGRQLSGSSLALTISLGVVEIE
           390        400        410        420        430
KGEPFDNQLNAADQLLYLAKANGRNRVYSDIMIQEGLQKIGLNG
```

US 8,581,045 B2

HYPERVIRULENT MUTANT OF AGROBACTERIUM TUMEFACIENS

CROSS REFERENCE TO RELATED APPLICATION

This application claims priority to U.S. Provisional Application No. 61/263,305 filed Nov. 20, 2009, herein incorporated by reference.

ACKNOWLEDGMENT OF GOVERNMENT SUPPORT

This invention was made with government support under R01 GM52465 awarded by The National Institutes of Health. The government has certain rights in the invention.

FIELD

This disclosure relates to a mutant *Agrobacterium tumefaciens* that is functionally deleted for the cyclic di-GMP synthase Atu1060 which renders the bacteria hypervirulent, as well as methods for its use in transforming plants with desired transgenes.

BACKGROUND

*Agrobacterium tumefaciens* causes tumors, called crown galls, by transferring to plant cells a small piece of DNA called T-DNA. In the bacterium, the T-DNA is part of a large virulence element called a Ti plasmid. This bacterium is the primary tool to transfer genes of agronomic benefit to plants of agricultural value including corn, soybean, cotton, rice, and wheat crops. Currently, derivatives of *A. tumefaciens* are used in which the T-DNA has been modified such that it lacks the tumor-inducing genes native to the system, and has added to it, the genes desired to be transfer to the plant.

Although *A. tumefaciens* strains are currently used, there are problems with the system. First, certain agriculturally-important plants are recalcitrant to gene introductions by the bacterium. Second other sets of plants can be transformed by *A. tumefaciens*, but the efficiencies are very low, making the development of transgenic derivatives of these plants an expensive and labor-intensive project.

Researchers have worked on improving the *Agrobacterium* system for transferring DNA to plants. Many studies have been directed towards developing conditions that improve the susceptibility of the plant to infection by *Agrobacterium*. Such approaches have proven useful in developing or improving transformation efficiencies in certain plants. From the perspective of the bacterium, most studies have focused on the Ti plasmid and on the genetic constructs, called binary plasmids, which carry the transgene. These two approaches have yielded limited successes. A third strategy has focused on mixing T-plasmids from one set of *Agrobacterium* isolates with the chromosomal background of other *Agrobacterium* isolates in an effort to identify combinations that are more effective than the natural pairings. With the exception of strain A281, and its derivatives EHA101 and EHA105, this approach has not been successful.

The development of a strain of *A. tumefaciens* that is significantly more efficient in transferring DNA to plant cells is thus needed for developing transformation systems for recalcitrant plant species and for improving the efficiency of transformation of plant species that are transformable at only low efficiencies.

SUMMARY

Herein provided is a novel mutant strain of *Agrobacterium tumefaciens* (*A. tumefaciens*). In particular examples, provided are isolated *A. tumefaciens* bacteria having the cyclic di-GMP synthase gene atu1060 functionally deleted. That is, the native di-GMP synthase gene atu1060 is disrupted such that the cyclic di-GMP synthase Atu1060 is not produced or protein which is produced does not have cyclic di-GMP synthase activity, thereby rendering the mutant bacteria hypervirulent. Methods of producing functional deletions are routine in the art. For example, recombinant *A. tumefaciens* bacteria are provided that have an exogenous nucleic acid molecule inserted into the atu1060 gene. In other examples, the atu1060 gene is rendered functionally deleted by removing all or part of the atu1060 gene sequence. In some examples, the disclosed mutant *A. tumefaciens* bacteria further include one or more transgenes (for example on a plasmid) that provides a benefit to a plant. Also provided are recombinant plant cells and plants that have had exogenous nucleic acids introduced therein using the disclosed mutant *A. tumefaciens* bacteria.

Methods of transforming plants using the disclosed mutant *A. tumefaciens* bacteria, for example to generate transgenic plants and plant cells, are provided. In particular examples the method includes contacting a plant cell with the disclosed mutant *A. tumefaciens* bacteria under conditions that permit the bacteria to attach to and transfer DNA to the plant cell. Also provided are transformed plant cells and plants produced by such methods.

The foregoing and other objects and features of the disclosure will become more apparent from the following detailed description.

BRIEF SUMMARY OF THE DRAWINGS

FIG. 2 shows the domain structure of Atu1060 (SEQ ID NO: 1). The Atu1060 protein contains two major domains. The first blocked region (amino acids 3-113) is a CheY-like domain that is associated with accepting signals from an upstream source via phosphorylation of an aspartate residue (D59, shown by the arrow). A mutation that changes D59 to an alanine abolishes Atu1060 activity. The second blocked region (amino acids 335-339) is a GGDEF domain and is the signature domain for enzymes that synthesize the intracellular signal cyclic di-GMP. The central amino acid residues are critical for synthesis of this signal. A mutation that changes E338 (shown by the arrow) to an alanine abolishes Atu1060 activity.

SEQUENCE LISTING

Figure 1:
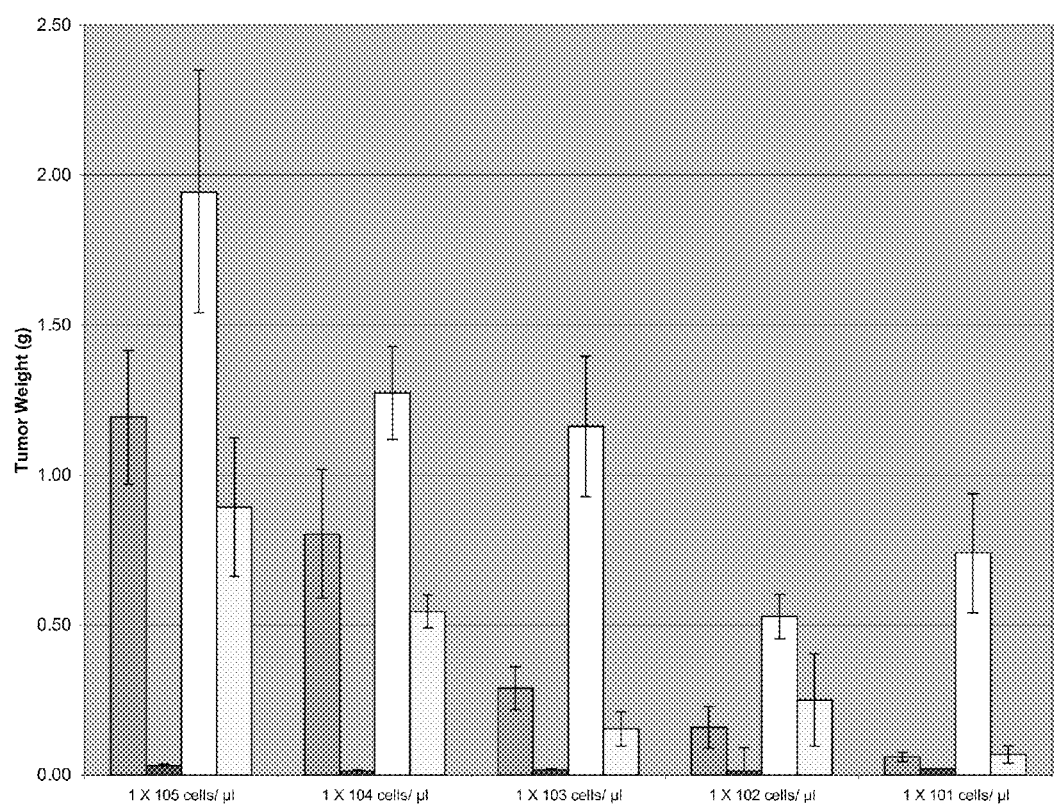
FIG. 1 is a bar graph showing the virulence (as indicated by tumor weight) following inoculation with different doses of the following strains (from left to right) wild type strain [NTL4(pTiC58)], the wild-type strain without a Ti plasmid [NTL4], the atu1060 deletion mutant [NTL4delta-atu1060 (pTiC58)] and the atu1060 mutant complemented with a wild-type allele of the atu1060 gene (i.e., the merodiploid atu1060 mutant/atu1060 wild type) [NTL4delta-atu1060/mTn7::atu1060(pTiC58)]. Each bar represents the average tumor weight from all 12 plants (4 plants, 3 experiments). The error bars represent standard error as determined by the Student T test.

The nucleic and amino acid sequences listed in the accompanying sequence listing are shown using standard letter abbreviations for nucleotide bases and amino acids. Only one strand of each nucleic acid sequence is shown, but the complementary strand is understood as included by any reference to the displayed strand.

SEQ ID NO: 1 is an exemplary Atu1060 amino acid sequence from NTL4, encoded by the nucleic acid sequence shown in SEQ ID NO: 2

SEQ ID NO: 2 is an exemplary atu1060 genomic sequence. The start codon is in bold. This sequence is the reverse complement of the gene sequence.

```
AGGCGTTTTTTGTGCCTAGAGACTAGAGCTGAGCGTTGCCGCGGCC

TTCAGCCGTTCAGCCCGATTTTCTGCAGGCCTTCCTGGATCATGAT

GTCGGAATAAACGCGGTTGCGGCCATTCGCCTTGGCGAGATAGAGC

AACTGATCCGCCGCATTCAGCTGGTTGTCGAAGGGCTCGCCCTTTT

CGATCTCCACGACACCGAGTGAAATTGTCAGTGCCAGGCTGCTGCC

GCTCAGCTGCCGGCCGTTCTTTTCCACCTGTTCGCGCAGTTCCTCG

CAGAAGGCATAGGCAGCCCGCGCATCCAGCCCTCGCAGGAACACGG

CAAATTCCTCACCGCCGAGGCGGGCGGGAATATGGCGTTGCTCGTC

GCACATGCCCTGCAGCAGTTCAGCCAGCTTCTTCAGCGCCCTGTCG

CCGGCATCGTGCCCTAGCGTGTCGTTGATCTTCTTGAAATGGTCAA

TGTCGAGAATGGCGACTGCGCCGCTCTCGTCATTGTCATTGATGAC

ATCCATCAGCGCGCGCGTGCGCTCGAAGAAGGAGCGGCGATTGGGC

AGGCCGGTGAGGTGGTCCCGTTCGGCCAGTTCACGCAGGCGCTTGA

GCTGCTTCAGTGTCTCGATATTGTTGTCGATGCGGCACTGCAATTC

TTCCGGTACGAAGGGGCGGTAGACGAAATCCGACGCGCCGGCCTTG

AGGAAGCTTGCCGAAAGCAGGCGGTCCGTGGAGGAGGATATGCCGA

TCACCCGCAGGTCTTCGGAGGACCTGCTGTCGCGGATGCGCCGTGT

CAGTTCATAACCGTCCATATCCGGCATGTGGTAATCGGTAATGACG

AGCTGGATTGACGGGTCCTGCGAGAGGATTTCCAGCGCCCGGTTGC

CCGAATGGGCTTCGCTGACCTTGAAATTCTGCCGCTCCAGAATTTC

CACGAGGCCGGAGCGTGCGGTGCGCGCATCATCGACCACCAGAACG

GAAAAACGCTTGTTGGTCATAATCCGGTCGACCGTCTTGACCACGG

CATCGACGGTGCGATGGCCGTCCTTGACGATATAGTCGATGATCTT

CTTTTCGGCATAACGCTTGCGCGCTTCCTCATCCACCGTTGCAGTG

AAGACGATGGCCGGCACCTTGCGCTCGGATAGAAGCGTCAGAATTT

CCCCCTTGGGCGCATCGGGCAGGTTGAGACCCGTCAGCGCCAGCGT

GAAATTATTGGCCTGCATCAGGGCATCGGCCTCGGCCATGCTGGCG

CAATGGACGACCTCGGCTTCCGTTTCATCCGAAAGCCGCGTCCTCA

GCAGCATGGAAAGCGCAACGGAATCTTCAATCAGAAGGATTTTATC

CTGCATGGCCGTCCCAAGCCCCCCTGGCCCGTCTCCCCAGTCTTTC

CTCAACGCCGAATATTCGTCATTCGCGTATCCGCGAATTCGAAGGC

CAGCTTATGCATTGTTGTGGAAAAAATGCGGAATAGAAAAGTTCTT

TTGTATTCACTAATC
```

DETAILED DESCRIPTION

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a transgene" includes single or plural transgenes and can be considered equivalent to the phrase "at least one transgene."

As used herein, the term "comprises" means "includes." Thus, "comprising a transgene" means "including a transgene" without excluding other elements. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references cited herein are incorporated by reference.

*Agrobacterium tumefaciens*: A Gram-negative bacterium that is the causative agent of crown gall disease. The DNA transmission capabilities of *Agrobacterium* can be used as a means of inserting foreign genes into plants.

atu1060: A gene that codes for an enzyme that coverts guanosine triphosphate (GTP) into the intracellular messenger molecule cyclic di-guanosine monophosphate (cyclic di-GMP). The term atu1060 includes any atu1060 gene, cDNA, or mRNA from *A. tumefaciens* that encodes an Atu1060 protein that can convert GTP into cyclic di-GMP, and when inactivated or disrupted in *A. tumefaciens*, results in hypervirulence of the mutated *A. tumefaciens* as described herein. It is shown herein that such functional deletion of the atu1060 gene in *A. tumefaciens* results in a bacterium that has increased virulence relative to parental *A. tumefaciens* strains.

Exemplary atu1060 sequences are provided in SEQ ID NOS: 1 and 2. However, one skilled in the art will appreciate that an atu1060 sequence can include orthologous sequences from *A. tumefaciens* (such as orthologous sequences from subspecies 1-9 of biovar1) that retain the ability to convert GTP into cyclic di-GMP, and when inactivated in *A. tumefaciens*, results in hypervirulence of the mutated *A. tumefaciens* as described herein.

Functional deletion: To attenuate the production of a gene product or the biological function of the gene product, for example by altering a gene sequence such that production of the gene product is significantly reduced (and in some cases eliminated) or the gene product produced is substantially or completely non-functional. Methods of making functional deletions are routine. As used herein, an atu1060 gene is said to be functionally deleted when the gene is altered (e.g., mutated) in any way such that the alteration disrupts the production or function of the protein product of the atu1060 gene in *A. tumefaciens* or atu1060 orthologs in other isolates of *A. tumefaciens*. For example, a functional deletion of a atu1060 in *A. tumefaciens* results in *A. tumefaciens* having substantially non-functional or non-existent Atu1060 protein, which results in hypervirulence of the mutant *A. tumefaciens* (e.g., less bacteria are required to transform plant cells than with the parental strain, for example as shown in FIG. 1).

Exemplary alterations/mutations that can be made to an atu1060 gene or ortholog thereof in order to render *A. tumefaciens* functionally deleted for this gene include (but are not limited to) nucleotide substitutions, partial or complete deletion of the nucleotide sequence, nucleotide insertions, or other variation. Particular examples include deletion of two or more nucleotides, up to and including all of the nucleotides within the open reading frame of the gene; insertion of a nucleotide sequence within the open reading frame of the gene; a combination of deletion and insertion of nucleotide sequence within the open reading frame (an indel); a deletion of a single nucleotide in the open reading frame of the gene that results in a frameshift in the coding register; an alteration in the nucleotide sequence within the open reading frame that results in creation of a premature stop codon which causes early termination of translation; one or more alterations in the nucleotide sequence of the open reading frame that result in substituting different amino acids at sites within the Atu1060 protein that are required for its activity and/or function. Other such alterations could include (but are not limited to) changes in the nucleotide sequence of the promoter region of the gene or of the ribosomal binding site of the gene that alter the transcription of the gene or the translation of the mRNA coded for by the gene. Yet other alterations could include (but are not limited to) changes in the gene sequence that encode one or both domains of Atu1060 shown in FIG. 2, thereby rendering the protein non-functional.

Hypervirulence: Increased virulence of a mutated bacterium, relative to the same strain of bacterium that is not mutated (e.g., the parental strain). For example, it is shown herein that by inactivating the atu1060 gene in *Agrobacterium tumefaciens* (e.g., functional deleting the atu1060 gene), the resulting *A. tumefaciens* has increased virulence as compared to the parental *A. tumefaciens* strain (e.g., NTL4 or NTL4 (pTiC58)). In some examples, mutant *A. tumefaciens* with a functionally deleted atu1060 gene are hypervirulent as indicated by their ability to induce tumors on a host plant (such as a tomato plant) at minimum infection doses at least 5-fold lower than those required by the parent strain. In some examples, mutant *A. tumefaciens* with a functionally deleted atu1060 gene are hypervirulent as indicated by their greater virulence towards a host plant (such as a tomato plant) than the virulence of the parent strain (such as NTL4 or NTL4 (pTiC58)), for example a virulence that is at least 2-fold greater (such as at least 3-fold, at least 4-fold, at least 5-fold, or at least 10-fold greater) than those of the parent strain, for example at a dose of $1 \times 10^1$ to $1 \times 10^3$ cells per μl.

Isolated: An "isolated" biological component (such as a nucleic acid molecule or protein) has been substantially separated, produced apart from, or purified away from other biological components in the cell of the organism in which the component occurs, for example, other chromosomal and extra-chromosomal DNA and RNA, and proteins. An "isolated" microorganism (such as a mutant *A. tumefaciens* bacterium) has been substantially separated or purified away from microorganisms of different types, strains, or species. Microorganisms can be isolated by a variety of techniques, including serial dilution and culturing.

Mutation: A change in a nucleic acid sequence (such as a gene sequence) or amino acid sequence, for example as compared to a nucleic acid or amino acid sequence present in a wild-type or parental organism. In particular examples, a mutation in atu1060 can increase the virulence of *A. tumefaciens*. Mutations can occur spontaneously, or can be introduced, for example using molecular biology methods. In particular examples, a mutation includes one or more nucleotide substitutions, deletions, insertions, or combinations thereof. In particular examples, the presence of one or more mutations in an atu1060 gene can functionally delete (for example significantly inactivate) that gene.

Orthologous genes: Corresponding genes in two genomes that encode proteins of the same function, are related to each other most recently by replicative cell division, and may have diverged slightly in nucleotide sequence from one another during evolutionary speciation. Thus, the disclosure includes mutant *A. tumefaciens* with a functionally deleted atu1060 gene as well as mutant *A. tumefaciens* with a functionally deleted ortholog of the atu1060 gene, such as atu1060 orthologs found in any of the nine subspecies (genomovars) of biovar 1 isolates of *A. tumefaciens*.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences are. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Mutant *Agrobacterium tumefaciens* (*A. tumefaciens*) Bacteria

The disclosure is directed to mutants of the bacterium *Agrobacterium tumefaciens* that induce tumors on host plants with an efficiency that is higher than that of the parent bacteria. The mutant exhibits an increased efficiency of transformation of several unrelated plant species indicating that the mutation affects the general gene transfer process and not factors influencing host specificity. Thus, the mutant is useful for improving the efficiency of introducing agronomically-important genes into a wide range of commercially important plants.

The mutant is defective in atu1060 (or ortholog thereof), which codes for an enzyme that coverts guanosine triphosphate (GTP) into the intracellular messenger molecule cyclic di-guanosine monophosphate (cyclic di-GMP). This molecule acts as an allosteric ligand that oftentimes alters the activity of proteins including certain enzymes. Thus the mutant is defective in a specific cyclic di-GMP synthase. However, bioinformatics analysis indicates that the *A. tumefaciens* genome, like those of most bacteria, encodes a large number of such enzymes. It is believed that each of these enzymes produces the small molecule messenger for a specific, and perhaps non-redundant, purpose or target. The mutation was constructed by site-directed mutagenesis. During the construction, a segment of the atu1060 gene was removed, and a gene cassette, encoding resistance to the antibiotic kanamycin, was inserted in its place. This indel (insertion-deletion) mutation was verified by polymerase chain reaction. One skilled in the art will appreciate that other changes to the gene sequence (such as other insertions and/or deletions) can be made to significantly reduce or even inhibit the biological activity of the encoded Atu1060 protein or significantly reduce the amount of Atu1060 protein produced (or even inhibit production of Atu1060 protein).

Since mutations in such cyclic di-GMP synthases, also called GGDEF proteins, often affect the intracellular organization, cell development, or cell surface properties of the bacterium, the atu1060 mutant was screened for alterations in phenotypes including production of extracellular polysaccharides, flagellar-based swimming motility, production of a hold-fast polysaccharide at the cell poles, and the ability to induce crown gall tumors on several host plants. The mutant showed no observable differences from wild-type in production of extracellular polysaccharides or motility.

However, the mutant *A. tumefaciens* with a functionally deleted atu1060 gene exhibited two novel phenotypes. First, it bound to glass slides in a polar fashion with much greater efficiency as compared to the wild-type parent (as determined by microscopy following application of a liquid culture of the bacteria to the surface of a glass microscope slide). In this respect, more cells of a population of the mutant expressed detectable polar hold-fast polysaccharide (as determined microscopically following staining of the cells with a fluorophore-labeled lectin that interacts specifically with the hold-fast polysaccharide) as compared to the parent. As shown in Table 1, greater numbers of mutant *A. tumefaciens* with a functionally deleted atu1060 gene attached to glass slides and showed polar lectin binding as compared to a wild-type strain of *A. tumefaciens*.

TABLE 1 atu1060 mutant shows increased polar binding to glass and an increase in the number of cells that produce the lectin-binding polysaccharide glue at their poles.

| Strain | Number (and %) of cells showing: | |
|---|---|---|
| | Glass slide attachment (%) | Polar lectin binding (%) |
| NTL4(pTiC58) | 9/272 (3.3) | 3/272 (1.1) |
| NTL4Δatu1060(pTiC58) | 49/209 (23.4) | 37/209 (17.7) |

Therefore, in some examples at least 10% (such as at least 15%, at least 20%, at least 21%, at least 22%, or at least 23%) of a mutant *A. tumefaciens* population with a functionally deleted atu1060 gene (or ortholog thereof) will show glass slide attachment, as compared to less than 10% (such as less than 5%, less than 4%, such as 1 to 5%) of wild-type *A. tumefaciens* (such as strain NTL4 or NTL4(pTiC58)). In some examples, the disclosed mutant bacteria attach to glass slides with greater efficiency than the same strain of *A. tumefaciens* bacterium having a functional cyclic di-GMP synthase atu1060 gene, for example in numbers at least 4-fold, at least 5-fold, at least 6-fold, or at least 7-fold greater than *A. tumefaciens* bacterium having a functional cyclic di-GMP synthase atu1060 gene. In some examples, the disclosed mutant bacteria demonstrate polar lectin binding with greater efficiency than the same strain of *A. tumefaciens* bacterium having a functional cyclic di-GMP synthase atu1060 gene, for example in numbers at least 4-fold, at least 5-fold, at least 6-fold, at least 7-fold, at least 10-fold, at least 12-fold or at least 15-fold greater than *A. tumefaciens* bacterium having a functional cyclic di-GMP synthase atu1060 gene.

Second, the mutant *A. tumefaciens* with a functionally deleted atu1060 gene (or ortholog thereof) induced tumors on two host plants, *Kalanchoe* and tomato, at minimum infection doses about 10-fold lower than those required by the parent. The experiment was done using four plants inoculated with each strain at each infection dose. The experiment was repeated twice (done a total of three times). Briefly, bacteria were grown overnight at 28° C. in MGL medium with appropriate antibiotics with shaking. The cells were collected by centrifugation for 10 minutes at 14000 rpm and the collected cells were resuspended in 1 ml of sterile 0.9% NaCl. The turbidity of the cell suspensions were measured at 600 nm using a Spectronic 20 spectrophotometer. The cell suspensions were standardized to $OD_{600}$ 1.0, then diluted in ten-fold increments from $10^{-2}$ to $10^{-6}$, corresponding to $10^5$ to $10^1$ cells per μL, based on cell counts from platings. Tomato plants (Sunny hybrid) were grown from seed for four weeks before inoculation. Shallow incisions (roughly 2-5 mm in length) were made in the stems at the first internode of the plant using a sterile knife. The wounds were inoculated with 2 μl volumes of the cell suspensions and the plant were grown in the greenhouse. After four weeks, the tumors were photographed, cut from the stems above and below the initial cut, measured for changes in length, and the segments were weighed for total mass. The specific tumor mass was determined by pushing the stem segment through a cork borer, removing the exposed tumor from the stem. The removed tumor mass was then weighed. Each condition represents data collected over three replicated procedures, with statistical analysis performed using the Student T-test.

As shown in FIG. 1, virulence, as measured by tumor weight on tomato stems, following inoculation with different doses ($1 \times 10^1$ to $1 \times 10^6$ cells per ul) of the wild type strain [NTL4(pTiC58)], the wild-type strain without a Ti plasmid [NTL4], the atu1060 deletion mutant [NTL4delta-atu1060 (pTiC58)] and the atu1060 mutant complemented with a wild-type allele of the atu1060 gene (i.e., the merodiploid atu1060 mutant/atu1060 wild type) [NTL4delta-atu1060/mTn7::atu1060(pTiC58)]. Therefore, in some examples, the disclosed mutant A. tumefaciens with a functionally deleted atu1060 gene (or ortholog thereof) induce tumors on a host plant (such as a tomato plant) at minimum infection doses at least 5-fold lower than those required by the parent strain (such as NTL4 or NTL4(pTiC58)), and in some examples lower than those required by strain NT1 or C58. In addition, in some examples, the disclosed mutant A. tumefaciens with a functionally deleted atu1060 gene (or ortholog thereof) have greater virulence towards a host plant (such as a tomato plant) than the virulence of the parent strain (such as NTL4 (pTiC58)), for example a virulence that is at least 2-fold greater (such as at least 3-fold, at least 4-fold, at least 5-fold, or at least 10-fold greater) than those of the parent strain, for example at a dose of $1 \times 10^1$ to $1 \times 10^3$ cells per μl (for example using 2 μl of such a dose).

Thus, the disclosed mutant A. tumefaciens with a functionally deleted atu1060 gene (or ortholog thereof) exhibits altered (e.g., increased) polar binding and an increased efficiency for causing crown gall tumors, which reflects a measure of the efficiency by which the bacterium transfers T-DNA to host plants. Interestingly, mutants in which three other cyclic di-GMP synthases were deleted (including the closely related gene celR) did not induce tumors on host plants with greater efficiency than the parent strain of A. tumefaciens (NTL4).

There is no other mutant of A. tumefaciens that exhibits the hypervirulent properties of the disclosed atu1060 mutant. The only other hypervirulent strain of A. tumefaciens described in the literature is A281. This strain is a derivative of a Ti-plasmid cured version of A. tumefaciens C58, called A136, into which the Ti plasmid of A. tumefaciens strain Bo542 was introduced. This strain, which mixes the chromosome of one A. tumefaciens strain with the Ti plasmid of another, produces larger crown gall tumors on several host plants as compared to either parent. The nature of the difference has been traced to a segment of the Ti plasmid (pTiBo542), although how this segment conditions virulence is not understood. A derivative of A281, called EHA105 that is suitable for use as a plant transformation agent has been developed.

Based on the identification of a strain of A. tumefaciens with greater virulence than wild-type A. tumefaciens strains (including C58) or other A. tumefaciens strains (such as NT1, which does not have the Ti plasmid, or NTL4 which lacks a Ti plasmid and which has two genes deleted and does not mutate to tetracycline resistance), the present disclosure provides an isolated A. tumefaciens bacterium, wherein the cyclic di-GMP synthase gene atu1060 in the bacterium is functionally deleted. In some examples, such mutant strains induce tumors on a host plants at minimum infection doses about 10-fold lower than those required by the parent NTL4(pTiC58).

Therefore, in some examples, the disclosed mutant bacteria induce tumors on a host plant (such as a tomato plant) at minimum infection doses at least 5-fold, at least 6-fold, at least 7-fold, at least 8-fold, at least 9-fold, at least 10-fold, at least 11-fold, at least 12-fold, at least 13-fold, at least 15-fold, or at least 15-fold lower than those required by the parent strain (such as NTL4(pTiC58)), and in some examples lower than those required by strain NT1(pTiC58) or C58. In some examples at least 10% (such as at least 12%, at least 15%, at least 18%, at least 20%, at least 21%, at least 22%, or at least 23%) of a mutant A. tumefaciens population with a functionally deleted atu1060 gene (or ortholog thereof) will attach to a glass slide, as compared to less than 10% (such as less than 5%, less than 4%, such as 1 to 5%) of wild-type A. tumefaciens (such as strain NTL4 or NTL4(pTiC58)). In addition, in some examples, the disclosed mutant A. tumefaciens with a functionally deleted atu1060 gene (or ortholog thereof) have greater virulence than the parent strain (such as NTL4 (pTiC58)) towards a plant, for example a virulence that is at least 2-fold greater (such as at least 3-fold, at least 4-fold, at least 5-fold, or at least 10-fold greater) than the virulence of the parent strain, for example at a dose of $1 \times 10^1$ to $1 \times 10^3$ cells per μl (such as a dose of $2 \times 10^1$ to $2 \times 10^3$ cells). The disclosed mutant bacteria can be recombinant, for example due to introduction of a non-native or exogenous nucleic acid sequence into the atu1060 gene sequence. Exemplary Atu1060 protein and gene sequences provided in SEQ ID NOS: 1 and 2, respectively.

A gene, such as atu1060 (or ortholog thereof), is functionally deleted when the function of the gene or gene product is significantly reduced or eliminated. Thus, 100% elimination is not required. For examples, a reduction in the amount of functional gene product (e.g., Atu1060 protein) expressed by the gene, or the biological activity of the gene (such as the ability to convert GTP into cyclic di-GMP) can be substantially reduced, for example a reduction of at least 50%, at least 70%, at least 80%, at least 90%, at least 95%, at least 98%, or at least 99%. In addition, functional deletion of atu1060, or an ortholog thereof, in A. tumefaciens results in hypervirulence of the mutated A. tumefaciens as described herein (for example by increasing the virulence of the A. tumefaciens by at least 5-fold relative to a parental strain in which atu1060 is not mutated and the bacterium produces functional Atu1060 protein). For example, genes can be functionally detected by deleting all or a portion of a gene from the organism (for example by removing all or part of the atu1060 gene, the regions on either side being joined together), by inserting another nucleic acid sequence into the gene, thereby disrupting the gene, or by combinations of both insertions and deletions. Other means by which to disrupt a gene are described herein and are known in the art. Such recombinant methods are well-known in the art, and can be used to disrupt an atu1060 gene in A. tumefaciens.

Based on the functional domains of Atu1060 (SEQ ID NO: 1; FIG. 2), one skilled in the art can mutate A. tumefaciens bacteria using recombinant methods by mutating the corresponding nucleic acid sequence, such that mutations are introduced that result in inactivation of the critical functional domains of the protein. As shown in FIG. 2, Atu1060 contains two major domains: the CheY-like domain (amino acids 3-113) and the GGDEF domain (amino acids 335-339). Thus, the atu1060 gene (or ortholog thereof) can be functionally deleted by mutating one or both of these regions, for example by deleting all of the nucleotides that encode one or both of these domains, by introducing other nucleotides into this region such that the function of the domain is inactivated, or by introducing mutations in one or more nucleotides that encode D59 (e.g., by making nucleotide substitutions that result in a D59A substitution) or E338 (e.g., by making nucleotide substitutions that result in an E338A substitution) can be performed to functionally delete atu1060. In other examples, the entire atu1060 coding sequence is deleted.

In one example, the mutant *A. tumefaciens* bacterium is *A. tumefaciens* strain NTL4 (Luo et al., *Mol Plant Microbe Interact.* 2001 January; 14(1):98-103, herein incorporated by reference) with the atu1060 gene functionally deleted. NTL4 is a "second derivative" of the wild-type tumorigenic strain C58. C58 is cured of its Ti plasmid to produce NT1 and the tetAR locus is deleted from NT1 to produce NTL4. NT1 and NTL4 are nonpathogenic because they lack a Ti plasmid (which can be reintroduced), and NTL4 does not mutate to resistance to tetracycline as do C58 and NT1. In other examples, the mutant *A. tumefaciens* bacterium is *A. tumefaciens* strain NT1 or C58 with the atu1060 gene functionally deleted. The Ti plasmid (which is deleted in the NT1 strain and the NTL4 strain) can be present or absent in the mutant *A. tumefaciens* bacterium with a functionally deleted atu1060 gene. In one example, the isolated *A. tumefaciens* bacteria disclosed herein is an *A. tumefaciens* biovar 1 (any of gemonovars 1-9) having atu1060 or an ortholog thereof functionally deleted, resulting in hypervirulence of the mutant relative to the parental strain as described herein. In one example the *A. tumefaciens* bacterium is NTL4, NT1, C58, GV2260, GV3101, GV3122, GV3166, GV3850, ACH5, EHA101, *A. tumefaciens* LBA4404 (genomovar 1), or EHA105 and other biovar1 strains of *A. tumefaciens* used for transforming plants, wherein their atu1060 gene or ortholog thereof is functionally deleted, which for example can increase the virulence of the resulting mutant bacteria. In one example, the isolated *A. tumefaciens* bacteria disclosed herein is an *Agrobacterium* radiobacter K84, a biovar 2 isolate having atu1060 or an ortholog thereof functionally deleted, resulting in hypervirulence of the mutant relative to the parental strain as described herein.

Orthologs of atu1060 can be identified based on functional and sequence similarity to SEQ ID NOS: 1 and 2. For example, functional deletion of an atu1060 ortholog will increase virulence of the resulting mutant *A. tumefaciens* bacteria. In some examples, orthologs of the Atu1060 protein retain the CheY-like domain (amino acids 3-113) and/or the GGDEF domain (amino acids 335-339) shown in FIG. 2 (and orthologs of atu1060 will encode such domains, though due to the degeneracy of the code, may vary from the sequence shown in SEQ ID NO: 1).

In some examples, the atu1060 gene functionally deleted in the *A. tumefaciens* mutant originally encoded an Atu1060 protein having at least 80% sequence identity (such as at least 82%, at least 85%, at least 90%, at least 92%, at least 93%, at least 94%, at least 95%, at least 96%, at least 97%, at least 98%, at least 99% or 100% sequence identity) to the amino acid sequence shown in SEQ ID NO: 1 prior to being functionally deleted (e.g., the organism expressed this native Atu1060 protein sequence prior to the functional deletion). In some examples, the atu1060 gene functionally deleted in the *A. tumefaciens* mutant originally had at least 80% sequence identity (such as at least 82%, at least 85%, at least 90%, at least 92%, at least 93%, at least 94%, at least 95%, at least 96%, at least 97%, at least 98%, at least 99% or 100% sequence identity) to the nucleic acid sequence shown in SEQ ID NO: 2 prior to being functionally deleted (e.g., the organism had this native atu1060 sequence present in its genome prior to the functional deletion). In some examples, the mutant *A. tumefaciens* bacteria do not have the nucleic acid sequence shown in SEQ ID NO: 2 present in its genome following the functional deletion of atu1060. In some examples, the mutant *A. tumefaciens* bacteria do not express detectable levels of the amino acid sequence shown in SEQ ID NO: 2 (or an ortholog thereof) present in its genome following the functional deletion of atu1060.

The mutant *A. tumefaciens* bacterium having a functionally deleted atu1060 in some examples also includes one or more transgenes that provides a benefit to a plant. Such transgenes can be introduced into the bacteria using routine methods, such as electroporation. In some examples, plasmids containing one or more transgenes are included in the mutant. Transgenes with desirable traits include those that provide a benefit to a plant, such as a commercially desirable, agronomically important trait. Examples include, but are not limited to: resistance to insects and other pests and disease-causing agents (such as viral, bacterial, fungal, and nematode agents, for example pests that cause rust or mildew); tolerance or resistance to herbicides; enhanced stability; increased yield or shelf-life; environmental tolerances (such as tolerance to drought, heat, chilling, freezing, excessive moisture, salt stress, or oxidative stress); and nutritional enhancements (such as starch quantity and quality; oil quantity and quality; protein quality and quantity; amino acid composition; and the like). Examples of such transgenes are well known in the art.

Methods of Using Mutant *A. tumefaciens* Bacteria with Hypervirulence

Also provided herein are methods of transforming a plant, such as a plant that has traditionally been recalcitrant to infection using currently available strains of *A. tumefaciens* bacteria. Such methods can be used to transfer a beneficial transgene into a plant, such as one or more of the transgenes described above. In such examples, the *A. tumefaciens* bacteria with a functionally deleted atu1060 gene would further include the desired transgene, for example on a plasmid that has been introduced into the bacteria.

Methods of using *A. tumefaciens* bacteria to transform plants are routine in the art (for example see the chapters concerning transformation of various plant and crop species using *A. tumefaciens* published in: *Methods in Molecular Biology* Vol 343 (2006) pp. 87-473). In particular examples, the method includes contacting a plant cell with *A. tumefaciens* bacteria having a functionally deleted atu1060 gene, under conditions that permit the bacterium to infect the plant cell. For example, plant cells in culture can be incubated with the mutant *A. tumefaciens* bacteria (for example 1 to 5 μl, such as 2 μl, of bacteria at a concentration of $1\times10^1$ to $1\times10^3$ cells per μl) under conditions that permit the bacteria to infect the cells. In other examples, the plant itself (such as a part thereof, such as a leaf) can be contacted with the mutant *A. tumefaciens* bacteria under conditions that permit that bacteria to infect the cells of the plant. In one example, at least 10-times less of the mutant *A. tumefaciens* bacteria are used than is traditionally used (or would need to be used) with other strains of mutant *A. tumefaciens* bacteria (such as NTL4, NT1 or L58). Methods of transforming plants with other strains of *A. tumefaciens* bacteria are well known in the field, and can be used with the currently described *A. tumefaciens* mutant (except that fewer bacteria are needed). One skilled in the art will appreciate that such methods can be used to transfer transgenes to any and all plant species of interest using the disclosed mutant bacteria.

Also provided are recombinant or transformed plant cells, and recombinant plants, that have been transformed with the mutant *A. tumefaciens* bacteria provided herein.

The disclosure is not limited to particular plants. One skilled in the art will appreciate that monocots and dicots can benefit from the disclosure. For example, the disclosed *A. tumefaciens* bacteria with a functionally deleted Atu1060 gene can be used in combination with crop plants (for example to introduce transgenes into such plants), such as corn, wheat, rice, soybeans, alfalfa, tomatoes, cotton, sugarcane, and canola. In one example the plant is a flowering plant. In one example the plant is a cereal, legume or woody plant.

EXAMPLE 1

The Diguanylate Cyclases PleD and Atu1060 Affect Exopolysaccharide Production, Virulence and Cellular Interaction of *Agrobacterium tumefaciens*

*Agrobacterium tumefaciens* competes within the nutrient-rich rhizosphere of plant roots by forming complex biofilms on the root surface. Biofilm formation allows *A. tumefaciens* cells to compete for limited resources in otherwise nutrient-poor soil. The process of producing this film requires two steps: 1) a strong attachment of individual bacteria to the root surface at one pole of the cell, and 2) aggregation of multiple cells to each other and the root. While the interactions of *Agrobacterium* cells with plants have been studied, little is known concerning the internal signals controlling when biofilm formation occurs. One possibility is through the secondary messenger cyclic diguanosine monophosphate (c-di-GMP), a small molecule used in a variety of signaling mechanisms in bacteria. In *Caulobacter crescentus*, a related α-proteobacterium, localization of the holdfast stalk to the cell pole depends, in part, on c-di-GMP produced by the diguanylate cyclase PleD. Given the phylogenetic relatedness between *C. crescentus* and *A. tumefaciens*, we examined the influence of PleD orthologs of *A. tumefaciens* strain NTL4 (pTiC58) on phenotypes including cell morphology, exopolysaccharide production, motility, and tumorigenicity.

Previously, we showed that overexpression of pleD and atu1060 in NTL4 resulted in increased flocculation, increased Congo red binding, changes in motility and chemotaxis and failure to produce tumors on *Kalanchoë* leaves. The pleD- and atu1060-overexpressing strains also displayed increased formation of star-shaped aggregates called rosettes. Overexpression of three other diguanylate cyclases—atu0826, atu2228 or atu4490—only had modest effects on colony morphology, indicating these proteins do not play a significant role in the cellular processes examined.

To further examine to role of pleD and atu1060 in *A. tumefaciens*, both genes were deleted by allelic replacement, exchanging the genes for gentamicin or kanamycin cassettes, respectively.

Both NTL4ΔpleD and NTL4Δ1060 showed no changes in colony morphology or liquid growth behavior, and both mutants displayed similar levels of Congo Red binding to exopolysaccharides as wild-type NTL4. The NTL4Δ1060 strain produced a larger zone of spreading than wild-type cells on both motility and chemotaxis agar plates, while NTL4ΔpleD showed a larger zone only on chemotaxis plates.

Both mutants remained tumorigenic, although NTL4Δ1060 produced larger tumors at lower inoculum densities as compared to wild-type NTL4 (see FIG. 1). Interestingly, the NTL4Δ1060 strain showed a higher frequency of forming rosettes compared to wild-type cells in B⁻ minimal media, a media that induces production of exopolysaccharides in *Rhizobium* species. NTL4Δ1060 cells frequently attached perpendicularly to the glass slide during microscopy. This behavior indicates that the atu1060 mutant is affected in polar attachment of the cells to surfaces and to each other (see Table 1).

Since the atu1060 mutation removed virtually all of the atu1060 gene, and since the nature of the mutation was verified in the NTL4 mutant, it is concluded that the mutant is not making any complete Atu1060 protein.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. An isolated *Agrobacterium tumefaciens* (*A. tumefaciens*) bacterium, wherein a cyclic di-GMP synthase atu1060 gene is functionally deleted.

2. The isolated *A. tumefaciens* bacterium of claim 1, wherein the bacterium is a recombinant bacterium comprising an exogenous nucleic acid molecule inserted into a cyclic di-GMP synthase atu1060 gene of the bacterium, thereby functionally deleting the cyclic di-GMP synthase atu1060 gene.

3. The isolated bacterium of claim 1, wherein the bacterium is *A. tumefaciens* strain NTL4, NT1, GV2260, GV3101, GV3122, GV3166, GV3850, ACH5, EHA101, EHA105, or C58.

4. The isolated bacterium of claim 1, wherein the isolated bacterium induces tumors on a host plant at a minimum infection dose at least 5-fold lower than those required by the same strain of *A. tumefaciens* bacterium having a functional cyclic di-GMP synthase atu1060 gene.

5. The isolated bacterium of claim 1, wherein the isolated bacterium attaches to glass slides with at least 4-fold greater efficiency than the same strain of *A. tumefaciens* bacterium having a functional cyclic di-GMP synthase atu1060 gene.

6. The isolated bacterium of claim 1, wherein the isolated bacterium demonstrates polar lectin binding with at least 4-fold greater efficiency than the same strain of *A. tumefaciens* bacterium having a functional cyclic di-GMP synthase atu1060 gene.

7. The isolated bacterium of claim 1, wherein the functional deletion is achieved by removal of at least a portion of the atu1060 gene.

8. The isolated bacterium of claim 1, wherein the atu1060 gene in a wild-type *A. tumefaciens* bacterium encodes a protein having at least 95% sequence identity to the amino acid sequence shown in SEQ ID NO: 1.

9. The isolated bacterium of claim 1, wherein the atu1060 gene in a wild-type *A. tumefaciens* bacterium comprises the nucleic acid sequence shown in SEQ ID NO: 2.

10. The isolated bacterium of claim 1, wherein the bacterium does not comprise a nucleic acid sequence comprising SEQ ID NO: 2.

11. The isolated bacterium of claim 1, wherein the bacterium does not comprise an amino acid sequence having at least 95% sequence identity to the amino acid sequence shown in SEQ ID NO: 1.

12. The isolated bacterium of claim 1, further comprising a transgene that provides a benefit to a plant.

13. The isolated bacterium of claim 12, wherein the transgene is a gene that confers resistance to a pest, drought, or herbicide.

14. A method of transforming a plant, comprising:
contacting a plant cell with the isolated bacterium of claim 1, under conditions that permit the bacterium to infect the plant cell, thereby transforming the plant.

15. The method of claim 14, wherein the plant cell is a corn cell, wheat cell, rice cell, soybean cell, alfalfa cell, tomato cell, cotton cell, or canola cell.

16. The isolated bacterium of claim 1, wherein the bacterium is an *A. tumefaciens* biovar 1 isolate.

17. The isolated bacterium of claim 16, wherein the bacterium is *A. tumefaciens* strain C58.

18. The isolated bacterium of claim 1, wherein the atu1060 gene in a wild-type *A. tumefaciens* bacterium encodes a protein having at least 92% sequence identity to the amino acid sequence shown in SEQ ID NO: 1.

19. The isolated bacterium of claim 1, wherein the bacterium does not comprise an amino acid sequence having at least 92% sequence identity to the amino acid sequence shown in SEQ ID NO: 1.

20. The isolated bacterium of claim 1, wherein the atu1060 gene in a wild-type *A. tumefaciens* bacterium comprises a nucleic acid sequence having at least 90% sequence identity to the nucleic acid sequence shown in SEQ ID NO: 2.

21. The isolated bacterium of claim 1, wherein the bacterium does not comprise a nucleic acid sequence having at least 90% sequence identity to the nucleic acid sequence shown in SEQ ID NO: 2.

\* \* \* \* \*

SEQUENCE LISTING

<160> NUMBER OF SEQ ID NOS: 2

<210> SEQ ID NO 1
<211> LENGTH: 430
<212> TYPE: PRT
<213> ORGANISM: Agrobacterium tumefaciens

<400> SEQUENCE: 1

```
Met Gln Asp Lys Ile Leu Leu Ile Glu Asp Ser Val Ala Leu Ser Met
1               5                   10                  15

Leu Leu Arg Thr Arg Leu Ser Asp Glu Thr Glu Ala Glu Val Val His
            20                  25                  30

Cys Ala Ser Met Ala Glu Ala Asp Ala Leu Met Gln Ala Asn Asn Phe
        35                  40                  45

Thr Leu Ala Leu Thr Gly Leu Asn Leu Pro Asp Ala Pro Lys Gly Glu
    50                  55                  60

Ile Leu Thr Leu Leu Ser Glu Arg Lys Val Pro Ala Ile Val Phe Thr
65                  70                  75                  80

Ala Thr Val Asp Glu Glu Ala Arg Lys Arg Tyr Ala Glu Lys Lys Ile
```

```
            85                  90                  95
Ile Asp Tyr Ile Val Lys Asp Gly His Arg Thr Val Asp Ala Val Val
            100                 105                 110
Lys Thr Val Asp Arg Ile Met Thr Asn Lys Arg Phe Ser Val Leu Val
            115                 120                 125
Val Asp Asp Ala Arg Thr Ala Arg Ser Gly Leu Val Glu Ile Leu Glu
            130                 135                 140
Arg Gln Asn Phe Lys Val Ser Glu Ala His Ser Gly Asn Arg Ala Leu
145                 150                 155                 160
Glu Ile Leu Ser Gln Asp Pro Ser Ile Gln Leu Val Ile Thr Asp Tyr
            165                 170                 175
His Met Pro Asp Met Asp Gly Tyr Glu Leu Thr Arg Arg Ile Arg Asp
            180                 185                 190
Ser Arg Ser Ser Glu Asp Leu Arg Val Ile Gly Ile Ser Ser Ser Thr
            195                 200                 205
Asp Arg Leu Leu Ser Ala Ser Phe Leu Lys Ala Gly Ala Ser Asp Phe
            210                 215                 220
Val Tyr Arg Pro Phe Val Pro Glu Glu Leu Gln Cys Arg Ile Asp Asn
225                 230                 235                 240
Asn Ile Glu Thr Leu Lys Gln Leu Lys Arg Leu Arg Glu Leu Ala Glu
            245                 250                 255
Arg Asp His Leu Thr Gly Leu Pro Asn Arg Arg Ser Phe Phe Glu Arg
            260                 265                 270
Thr Arg Ala Leu Met Asp Val Ile Asn Asp Asn Asp Glu Ser Gly Ala
            275                 280                 285
Val Ala Ile Leu Asp Ile Asp His Phe Lys Lys Ile Asn Asp Thr Leu
            290                 295                 300
Gly His Asp Ala Gly Asp Arg Ala Leu Lys Lys Leu Ala Glu Leu Leu
305                 310                 315                 320
Gln Gly Met Cys Asp Glu Gln Arg His Ile Pro Ala Arg Leu Gly Gly
            325                 330                 335
Glu Glu Phe Ala Val Phe Leu Arg Gly Leu Asp Ala Arg Ala Ala Tyr
            340                 345                 350
Ala Phe Cys Glu Glu Leu Arg Glu Gln Val Glu Lys Asn Gly Arg Gln
            355                 360                 365
Leu Ser Gly Ser Ser Leu Ala Leu Thr Ile Ser Leu Gly Val Val Glu
            370                 375                 380
Ile Glu Lys Gly Glu Pro Phe Asp Asn Gln Leu Asn Ala Ala Asp Gln
385                 390                 395                 400
Leu Leu Tyr Leu Ala Lys Ala Asn Gly Arg Asn Arg Val Tyr Ser Asp
            405                 410                 415
Ile Met Ile Gln Glu Gly Leu Gln Lys Ile Gly Leu Asn Gly
            420                 425                 430

<210> SEQ ID NO 2
<211> LENGTH: 1487
<212> TYPE: DNA
<213> ORGANISM: Agrobacterium tumefaciens

<400> SEQUENCE: 2
aggcgttttt tgtgcctaga gactagagct gagcgttgcc gcggccttca gccgttcagc     60
ccgattttct gcaggccttc ctggatcatg atgtcggaat aaacgcggtt gcggccattc    120
gccttggcga gatagagcaa ctgatccgcc gcattcagct ggttgtcgaa gggctcgccc    180
ttttcgatct ccacgacacc gagtgaaatt gtcagtgcca ggctgctgcc gctcagctgc    240
```

-continued

```
cggccgttct tttccacctg ttcgcgcagt tcctcgcaga aggcataggc agcccgcgca    300
tccagccctc gcaggaacac ggcaaattcc tcaccgccga ggcgggcggg aatatggcgt    360
tgctcgtcgc acatgccctg cagcagttca gccagcttct tcagcgccct gtcgccggca    420
tcgtgcccta gcgtgtcgtt gatcttcttg aaatggtcaa tgtcgagaat ggcgactgcg    480
ccgctctcgt cattgtcatt gatgacatcc atcagcgcgc gcgtgcgctc gaagaaggag    540
cggcgattgg gcaggccggt gaggtggtcc cgttcggcca gttcacgcag gcgcttgagc    600
tgcttcagtg tctcgatatt gttgtcgatg cggcactgca attcttccgg tacgaagggg    660
cggtagacga aatccgacgc gccggccttg aggaagcttg ccgaaagcag gcggtccgtg    720
gaggaggata tgccgatcac ccgcaggtct tcggaggacc tgctgtcgcg gatgcgccgt    780
gtcagttcat aaccgtccat atccggcatg tggtaatcgg taatgacgag ctggattgac    840
gggtcctgcg agaggatttc cagcgcccgg ttgcccgaat gggcttcgct gaccttgaaa    900
ttctgccgct ccagaatttc cacgaggccg gagcgtgcgg tgcgcgcatc atcgaccacc    960
agaacggaaa aacgcttgtt ggtcataatc cggtcgaccg tcttgaccac ggcatcgacg    1020
gtgcgatggc cgtccttgac gatatagtcg atgatcttct tttcggcata acgcttgcgc    1080
gcttcctcat ccaccgttgc agtgaagacg atggccggca ccttgcgctc ggatagaagc    1140
gtcagaattt cccccttggg cgcatcgggc aggttgagac ccgtcagcgc cagcgtgaaa    1200
ttattggcct gcatcagggc atcggcctcg gccatgctgg cgcaatggac gacctcggct    1260
tccgtttcat ccgaaagccg cgtcctcagc agcatggaaa gcgcaacgga atcttcaatc    1320
agaaggattt tatcctgcat ggccgtccca agcccccctg gcccgtctcc ccagtctttc    1380
ctcaacgccg aatattcgtc attcgcgtat ccgcgaattc gaaggccagc ttatgcattg    1440
ttgtggaaaa aatgcggaat agaaaagttc ttttgtattc actaatc                 1487
```